United States Patent
Shibayama et al.

(10) Patent No.: US 8,160,821 B2
(45) Date of Patent: *Apr. 17, 2012

(54) METHOD FOR SUPPORTING A DIAGNOSIS OF AN EFFECT OF A TREATMENT BY USING ANTHRACYCLINE ANTICANCER DRUGS AND A DEVICE FOR SUPPORTING A DIAGNOSIS FOR AN EFFECT OF A TREATMENT BY USING ANTHRACYCLINE ANTICANCER DRUGS

(75) Inventors: Masaki Shibayama, Kobe (JP); Hideki Ishihara, Miki (JP); Tomoko Matsushima, Kobe (JP); Shigehiro Numada, Kobe (JP)

(73) Assignee: Sysmex Corporation, Hyogo (JP)

( * ) Notice: Subject to any disclaimer, the term of this patent is extended or adjusted under 35 U.S.C. 154(b) by 673 days.

This patent is subject to a terminal disclaimer.

(21) Appl. No.: 12/242,500

(22) Filed: Sep. 30, 2008

(65) Prior Publication Data

US 2009/0248316 A1 Oct. 1, 2009

(30) Foreign Application Priority Data

Mar. 28, 2008 (JP) ................................ 2008-086213

(51) Int. Cl.
*G06F 19/00* (2011.01)
*G06F 15/00* (2006.01)
*C12Q 1/25* (2006.01)

(52) U.S. Cl. .................................. 702/23; 700/1; 435/4

(58) Field of Classification Search ....................... None
See application file for complete search history.

(56) References Cited

U.S. PATENT DOCUMENTS

| 2006/0017362 A1 | 1/2006 | Uno et al. |
| 2007/0003438 A1 | 1/2007 | Kobayashi et al. |
| 2007/0231837 A1 | 10/2007 | Ishihara et al. |

OTHER PUBLICATIONS

Ishihara et al. A new cancer diagnostic system based on a CDK profiling technology. Biochimica et Biophysica Acta vol. 1741, pp. 226-233 (2005).*

* cited by examiner

*Primary Examiner* — John S Brusca
(74) *Attorney, Agent, or Firm* — Sughrue Mion, PLLC

(57) ABSTRACT

A method of supporting a diagnosis of an effect of a treatment by using anthracycline anticancer drugs is disclosed. The method provides a new value for judging an effect, a judgment score, which is calculated based on expression levels and activity values of two cyclin dependent kinases (CDKs). The effect of the treatment by using anthracycline anticancer drugs is judged by comparing the judgment score with a predetermined threshold level.

14 Claims, 9 Drawing Sheets

METHOD FOR SUPPORTING A DIAGNOSIS OF AN EFFECT OF A TREATMENT BY USING ANTHRACYCLINE ANTICANCER DRUGS AND A DEVICE FOR SUPPORTING A DIAGNOSIS FOR AN EFFECT OF A TREATMENT BY USING ANTHRACYCLINE ANTICANCER DRUGS

FIELD OF THE INVENTION

The present invention relates to a method for supporting a diagnosis of an effect of a treatment by using anthracycline anticancer drugs, and a device for supporting a diagnosis of an effect of a treatment by using anthracycline anticancer drugs.

BACKGROUND

Conventionally, chemotherapy, that is, therapy by using anticancer drugs has been conducted as one of therapies for cancer patients. The anticancer drug treatment is a treatment method that is extremely useful for prevention of cancer progress or cancer recurrence, but is accompanied by risks due to side effects.

The anticancer drug is also known to differ in effectiveness from one patient to another. While some patients must take risks due to side effects, there are many patients who can, depending on the anticancer drug, not obtain a sufficient anticancer effect. To solve this problem, an approach for providing the maximum anticancer drug treatment by predicting an effect of an anticancer drug in a cancer patient (the sensitivity of the patient to the anticancer drug) while avoiding risks due to unnecessary side effects has been proposed.

For example, US 2007/0231837, US 2006/0173632 or US 2007/0003438 describes a method for judging sensitivity to a taxane-based anticancer drug on the basis of the activity value and expression level of a cyclin-dependent kinase (CDK).

The anticancer drug is known to differ in action on the living body depending on its type. For example, the taxane-based anticancer drug stabilizes intracellular microtubules in a polymerized state thereby suspending cellular mitosis to induce apoptosis. Peripheral neuritis is known as a major side effect of the taxane-based anticancer drug. An anthracycline-based anticancer drug, on the other hand, is known as an anticancer drug having an inhibitory action on topoisomerase. The anthracycline-based anticancer drug is a highly aggressive anticancer drug that directly destroys DNA, and causes severe side effects such as cardiac sarcolemma destruction and congestive heart failure. It follows that in treatment by using the anthracycline-based anticancer drug, it has been an important task to predict its usefulness in advance.

The present invention provides a novel method, being a nonconventional novel method, capable of highly accurately predicting an effect of treatment by using an anthracycline-based anticancer drug.

SUMMARY OF THE INVENTION

A first aspect of the invention is a method for supporting a diagnosis of an effect of a treatment by using anthracycline anticancer drugs, comprising: acquiring an expression level of a first cyclin dependent kinase (CDK), an activity value of the first CDK, an expression level of a second CDK and an activity value of the second CDK from a malignant tumor collected from a cancer patient to be examined; calculating a judgment score based on the following formula (1):

$$\text{judgment score} = F(x) \times G(y) \tag{1}$$

wherein x represents a first CDK specific activity which is able to be calculated by using a ratio of the expression level and the activity value of the first CDK, and y represents a specific activity ratio which is able to be calculated by using a ratio of the first CDK specific activity and a second CDK specific activity wherein the second CDK specific activity is able to be calculated by using a ratio of the expression level and the activity value of the second CDK.

A second aspect of the invention is a method for supporting a diagnosis of an effect of a treatment by using anthracycline anticancer drugs, comprising: acquiring an expression level of a first cyclin dependent kinase (CDK), an activity value of the first CDK, an expression level of a second CDK and an activity value of the second CDK from a malignant tumor collected from a cancer patient to be examined; calculating a first CDK specific activity which is able to be calculated by using a ratio of the expression level and the activity value of the first CDK, and a second CDK specific activity which is able to be calculated by using a ratio of the expression level and the activity value of the second CDK; and displaying a judgment graph which comprises at least two parameters of a first CDK specific activity and a second CDK specific activity, and is divided into zones different in judgment score calculated based on following formula (2), wherein the cancer patient to be examined is plotted based on the first CDK specific activity and the second CDK specific activity on the judgment graph, $$\text{judgment score} = F(x) \times G(y) \tag{2}$$

wherein x represents a first CDK specific activity; and y represents a specific activity ratio which is able to be calculated by using a ratio of the first CDK specific activity and the second CDK specific activity.

A third aspect of the invention is a device of supporting a diagnosis of an effect of a treatment by using anthracycline anticancer drugs, comprising: measuring section for measuring a malignant tumor collected from a cancer patient to be examined to acquire an expression level of a first cyclin dependent kinase (CDK), an activity value of the first CDK, an expression level of a second CDK and an activity value of the second CDK; and a controller including a memory under the control of a processor, the memory storing instructions enabling the processor to carry out operations which comprise calculating a judgment score based on the following formula (3):

$$\text{judgment score} = F(x) \times G(y) \tag{3}$$

wherein x represents a first CDK specific activity which is able to be calculated by using a ratio of the expression level and the activity value of the first CDK, and y represents a specific activity ratio which is able to be calculated by using a ratio of the first CDK specific activity and the second CDK specific activity wherein the second CDK specific activity is able to be calculated by using a ratio of the expression level and the activity value of the second CDK.

A fourth aspect of the invention is a device for supporting a diagnosis of an effect of a treatment by using anthracycline anticancer drugs, comprising: measuring section for measuring a malignant tumor collected from a cancer patient to be examined to acquire an expression level of a first cyclin dependent kinase (CDK), an activity value of the first CDK, an expression level of a second CDK and an activity value of the second CDK; a display; and a controller including a memory under the control of a processor, the memory storing instructions enabling the processor to carry out operations comprising: calculating a first CDK specific activity and a second CDK specific activity of the cancer patient to be examined based on the measurement results by the measurement section, wherein the first CDK specific activity is able to be calculated by using a ratio of the expression level and the activity value of the first CDK, and second CDK specific activity is able to be calculated by using a ratio of the expression level and the activity value of the second CDK; displaying a judgment graph which comprises at least two parameters of a first CDK specific activity and a second CDK specific activity, and is divided into zones different in judgment score calculated based on following formula (4), wherein the cancer patient to be examined is plotted based on the first CDK specific activity and the second CDK specific activity on the judgment graph, $$judgment\ score = F(x) \times G(y) \qquad (4)$$

wherein x represents a first CDK specific activity, and y represents a specific activity ratio which is able to be calculated by using a ratio of the first CDK specific activity and the second CDK specific activity.

DETAILED DESCRIPTION OF THE PREFERRED EMBODIMENTS

Figure 1A:
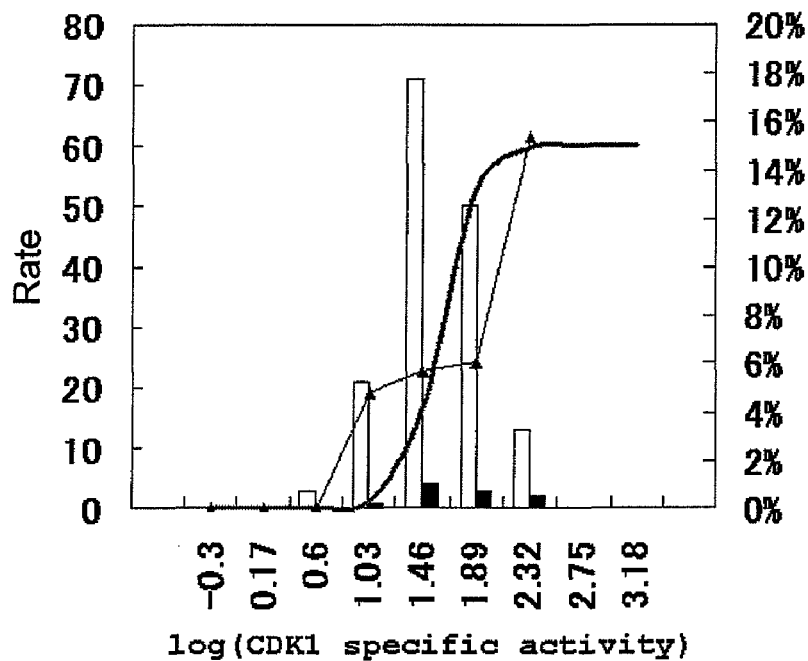
FIG. 1A is a histogram showing the relationship between the CDK1 specific activity obtained from a plurality of cancer patients to be examined and the cancer recurrence rate.

[1] Method for Determining an Effect of a Treatment by Using an Anthracycline-Based Anticancer Drug The judgment method in a first aspect of the invention is a method of determining an effect of a treatment by using an anthracycline-based anticancer drug, comprising acquiring expression levels and activity values of a first cyclin dependent kinase (CDK) and a second CDK from a malignant tumor collected from a cancer patient to be examined, determining a judgment score based on the obtained expression levels and activity values of the first CDK and the second CDK, and determining the effect of a treatment by using an anthracycline-based anticancer drug based on the obtained judgment score.

The "cancer" in this specification includes an epidermal cell cancer, a hematopoietic organ-derived cancer, a sarcoma, and the like. The type of cancer includes breast cancer, stomach cancer, colon cancer, esophageal cancer, prostate cancer, leukemia, osteosarcoma, and the like.

The "anticancer drug" in this specification refers to a chemical substance having an anticancer effect on the above-mentioned cancers.

The anthracycline-based anticancer drug in this specification refers to a group of antibiotics each having 1 to 3 amino acids or a neutral carbohydrate bound to anthracycline, or an aglycone. Examples of the anthracycline anticancer drug include daunorubicin, doxorubicin, aclarubicin, epirubicin, bleomycin, and the like.

The "recurrence" in this specification refers to a case where after an organ is partially eliminated for extirpating a malignant tumor, the same malignant tumor reappears in the remaining organ, and also to a case where a cancerous cell is separated from a primary tumor and carried into a distant tissue (distant organ) and proliferates autonomically therein.

The "risk of recurrence" in this specification means the risk of cancer recurrence in the body of a cancer patient from whom a malignant tumor has been extirpated, and the risk of death of the patient by cancer recurrence. Unless otherwise noted, the "risk of recurrence" includes both the risks.

(1) Step of Acquiring the Expression Levels and Activity Values of the First CDK and the Second CDK from a Malignant Tumor Collected from a Cancer Patient to be Examined Malignant tumors collected from cancer patients to be examined may be for example cells constituting supporting tissues in biological tissues of the patients, such as fibrous connective tissue, cartilage tissue, bone tissue, blood and lymph; epithelium tissue; muscle tissue; and nervous tissue. Particularly, the cell used in the judgment method in this embodiment is preferably a cell from which pathological information is to be obtained, such as a tumor cell derived from the tissue which dysfunctions in growth regulation and results in breaking a balance in an individual. Preferable examples of the tumor cell include a cell derived from a tumor generated in organs such as breast, lung, liver, stomach, colon, pancreas, skin, uterus, testis, ovary, thyroid gland, parathyroid gland, lymphatic system, and bone marrow.

The cyclin dependent kinase (CDK) is a generic term for various enzymes activated by binding to cyclin, and does not have an activity by itself, but becomes an activated form by binding to cyclin. The CDK acts in a specific phase of a cell cycle depending on its kind. The CDK includes CDK1, CDK2, CDK4, CDK6, cyclin A dependent kinase, cyclin B dependent kinase, and cyclin D dependent kinase.

From plural kinds of CDKs listed herein, a first CDK and a second CDK are determined, and the expression levels and activity values of the first CDK and the second CDK of a malignant tumor collected from a cancer patient to be examined are measured.

The CDK activity value refers to kinase activity level (U) which is calculated from an amount of a substrate to be phosphorylated upon the binding of CDK to a specific cyclin.

The substrate to be phosphorylated with the CDK includes histone H1 for activated CDK1 and activated CDK2 as well as Rb (retinoblastoma protein) for activated CDK4 and activated CDK6.

The CDK activity value can be measured by any conventional method of measuring CDK activity. Specifically, there is a method which comprises preparing a sample containing activated CDK from a cell lysate as a measurement sample, then using the sample and $^{32}$P-labeled ATP ($\gamma$-[$^{32}$P]-ATP) so that a substrate protein is allowed to incorporate $^{32}$P, measuring the labeling amount of the phosphorylated substrate labeled with $^{32}P$, and quantitatively determining the activity values based on a standard curve previously prepared using standard samples. As a method using no radioactive substance, there is a method which comprises preparing a sample containing activated CDK of interest from a cell lysate as a sample, reacting the substrate in the sample with adenosine 5'-O-(3-thiotriphosphate) (ATP-γS) to introduce a monothiophosphate group into a serine or threonine residue in the substrate protein, labeling the substrate by binding a fluorescent substance or a labeled enzyme to a sulfur atom in the introduced monothiophosphate group, measuring the amount of the labeled thiophosphorylated substrate (or the amount of the fluorescent substance in a case where the fluorescent substance is used), and quantitatively determining the phosphoric acid amount in the sample based on a standard curve previously prepared using standard samples.

US 2002/0164673 is hereby incorporated by reference in its entirely as though fully and completely set forth herein.

Samples subjected to activity measurement are prepared by specifically collecting CDK of interest from lysates of tissues containing malignant tumors to be measured. The sample may be prepared by using an anti-CDK antibody specific to CDK of interest. In the case where the activity of a specific cyclin dependent kinase (for example, cyclin A dependent kinase, cyclin B dependent kinase or cyclin E dependent kinase) is measured, the sample may be prepared using an anti-cyclin antibody. In both cases, CDK other than activated CDK is contained in the sample. For example, the cyclin-CDK complex to which a CDK inhibitor is bound may also be contained in the sample. When the anti-CDK antibody is used, CDK itself, a CDK-cyclin complex, a CDK-CDK inhibitor complex, and/or complexes of CDK and other compounds are contained. Accordingly, CDK activity value is measured in terms of the unit (U) of the phosphorylated substrate under the condition where various CDKs such as activated CDK, inactivated CDK, and various competitive reactions co-exist.

The CDK expression level is an amount of target CDK (unit corresponding to the number of molecules), which is contained in a cell lysate from tissues containing malignant tumors to be measured, and can be measured by a known method of measuring the amount of a target protein in a protein mixture. For example, an ELISA method or a Western blot process may be used. The target protein (CDK) can be captured by using a specific antibody. For instance, an anti-CDK1 antibody can be used to capture all CDK1s present in cells (for example, CDK itself, a CDK-cyclin complex, a CDK-CDK inhibitor complex, and/or complexes of CDK and other compounds).

US 2004/0214180 is hereby incorporated by reference in its entirely as though fully and completely set forth herein.

(2) Step of Calculating Judgment Score

Judgment score S is determined on the basis of the expression levels and activity values of the two CDKs obtained in the above step. The judgment score S is determined according to the following formulas (5) to (7):

$$S=F(x) \times G(y) \quad (5)$$

$$F(x)=a/(1+\mathrm{Exp}(-(x-b) \times c)) \quad (6)$$

$$G(y)=d/(1+\mathrm{Exp}(-(y-e) \times f)) \quad (7)$$

wherein a to f represent a constant.

In the formulas above, x represents the specific activity of the first CDK, and y represents the specific activity ratio. The CDK specific activity is expressed as the CDK activity value/CDK expression level. The specific activity ratio is expressed as the second CDK specific activity/first CDK specific activity. The formulas (5) to (7), the specific activity and the specific activity ratio will be described later in more detail.

(3) Step of Judging an Effect of a Treatment by Using an Anticancer Drug Based on a Judgment Score The judgment score S obtained as described above is compared with a predetermined threshold value to determine the effect of a treatment by using an anthracycline-based anticancer drug. The judgment score S of a cancer patient to be examined can be compared with a threshold value to determine the effect of a treatment by using an anthracycline-based drug; for example, when the judgment score S of the cancer patient to be examined is higher than the threshold value, the effect of the treatment by using the anthracycline-based anticancer drug in the cancer patient can be determined to be high, while when the judgment score S of the cancer patient to be examined is lower than the threshold value, the effect of the treatment by using the anthracycline-based anticancer drug in the cancer patient can be determined to be low.

The threshold value is a value suitably established depending on the type of anticancer drug and the type of cancer. Specifically, the threshold value can be the judgment score S which as a result of examination of the relationship between the therapeutic effect of an anthracycline-based anticancer drug administered to tumor cancers and the judgment score S, was determined so as to enable discrimination between cancer patients for whom treatment with the anthracycline-based anticancer drug is effective and those for whom the treatment is not effective.

By establishing the threshold value on the basis of actual clinical therapeutic results, the effect of anticancer drug treatment can be highly accurately determined.

Now, the formulae (5) to (7) are described.

First, the meanings of the CDK specific activity and specific activity ratio are described.

The CDK specific activity is expressed as the CDK activity value/CDK expression level and thus refers to the ratio of the activity value to the expression level of CDK. The CDK specific activity is a parameter that reflects the CDK enzyme activity per unit CDK protein mass contained in a sample, corresponds to the ratio of active CDK to CDK present in cells, and shows the CDK activity level based on the proliferating state of malignant tumor cells to be judged.

The specific activity ratio is expressed as the second CDK specific activity/first CDK specific activity and thus refers to the ratio of the second CDK specific activity to the first CDK specific activity. The CDK specific activity ratio is the ratio between the activity levels of two CDKs each exhibiting an activity in a specific cell cycle, and is a parameter that reflects which of the CDK activities in cancer patient's cells is predominant (which degree of cells is in which stage of cell cycle).

Generally, since a cancer cell is out of normally controlled growth and proliferates rapidly, when the ratio of cells staying in the period between S phase (DNA replicative period) and G2 phase (period of from termination of DNA synthesis to initiation of mitotic division) is high, the cells can be estimated to become cancerous. The aneuploidy is considered to be caused by passing through an abnormal M phase (cell division stage), or proceeding to G1 phase and then S phase without undergoing M phase. Therefore, the sample in which the ratio of cells in M phase is low may be estimated to become cancerous.

Accordingly, for example, CDK1 showing an activity during shifting from G2 phase to M phase in cell cycle is herein used as the first CDK, and CDK2 showing an activity during shifting from G1 phase to S stage in cell cycle is herein used as the second CDK. The CDK specific activity ratio determined based on the two CDKs is a numerical value reflecting how much the cells in the S or G2 phase occur relative to the cells in the M phase, and this numerical value can be used as a parameter accurately reflecting the proliferating ability of the cells.

Then, the formulae (5) to (7) for calculating the judgment score S are described.

As illustrated above, the parameter correlated with the proliferating ability of cells (risk of caner recurrence) can be obtained by obtaining the CDK specific activity ratio based on the first CDK specific activity and the second CDK specific activity.

However, there can be cases where the CDK specific activity ratio is not correlated with the proliferating ability of cells (risk of cancer recurrence). For example, when the CDK specific activity ratio is determined by using CDK1 as the first CDK and CDK2 as the second CDK as illustrated above, the CDK specific activity ratio is low when the CDK1 specific activity is abnormally high, but from another viewpoint, this low ratio can also be considered attributable to abnormal activation of CDK1 by high expression of cyclin that has formed a complex with CDK1.

It is considered that even if the amount of CDK activated in a certain cell cycle is low, cells can proliferate by compensatory function of another specific CDK, so abnormal activation of specific CDK can be also considered attributable to abnormal cellular kinetics.

Accordingly, the inventors have estimated that a risk of cancer recurrence can be determined by two risk factors: (1) first CDK specific activity and (2) second CDK/first CDK specific activity ratio, and they have decided to evaluate a risk of cancer recurrence based on these risk factors. The probabilities of cancer recurrence based on the risk factors (1) and (2) respectively are expressed as risk score RS (1) and risk score RS (2) using numerically evaluated scales. The probability of cancer recurrence resulting from the risk factors (1) and (2) is expressed as recurrence risk score RRS using a numerically evaluated scale. As a consequence, the probability of cancer recurrence (recurrence risk) is given by a product obtained by multiplying the probability of cancer recurrence resulting from the risk factor (1) by the probability of cancer recurrence from the risk factor (2), and therefore, the recurrence risk score RRS is given by a value proportional to the product of the risk score RS (1) and the risk score RS (2). Accordingly, the following formula can hold:

$$RRS=RS(1)\times RS(2) \quad (8)$$

The risk score RS (1) and risk score RS (2) can be determined in the following manner.

Figure 1B:
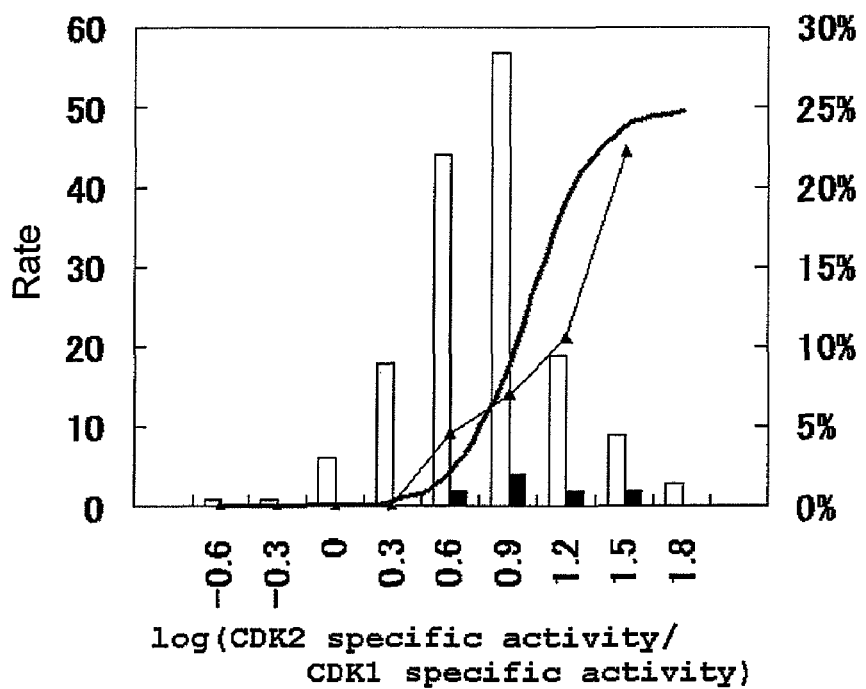
FIG. 1B is a histogram showing the relationship of the specific activity ratio between CDK1 and CDK2 from a plurality of cancer patients to be examined, to the cancer recurrence rate.

FIG. 1A is a histogram showing the relationship between the CDK1 specific activity obtained from a plurality of cancer patients to be examined and their cancer recurrence rate, and FIG. 1B is a histogram showing the relationship between the CDK2/CDK1 specific activity ratio obtained from a plurality of cancer patients and their cancer recurrence rate. In this graph, a plurality of cancer patients to be examined are classified according to the CDK1 specific activity or the CDK2/CDK1 specific activity ratio obtained from the cancer patients to be examined, and the total number of patients contained in each class is shown in white bar, and the number of patients having recurrence contained in each class is shown in shaded bar. Further, the probability of cancer recurrence (number of patients having recurrence/total number of patients) in each case is shown in line graph.

As can be seen from the graph, the probability of cancer recurrence is flatly increased according to the CDK1 specific activity or the CDK2/CDK1 specific activity ratio. Accordingly, the probability of cancer recurrence in each class can be approximated, thereby giving risk score RS (1) having the CDK1 specific activity as risk factor and risk score RS (2) having the CDK2/CDK1 specific activity ratio as risk factor. Accordingly, the probability of cancer recurrence in each class is approximated by logistic function wherein the CDK1 specific activity is expressed as x, and the CDK2/CDK1 specific activity ratio is expressed as y, whereby the risk score RS (1) and risk score RS (2) can be obtained. That is, the risk score RS (1) and risk score RS (2) are expressed respectively by the following formula:

$$RS(1); F(x)=a/(1+\text{Exp}(-(x-b)\times c)) \quad (8)$$

$$RS(2); G(y)=d/(1+\text{Exp}(-(y-e)\times f)) \quad (9)$$

wherein a to f represent a constant.

The recurrence risk score RRS determined by the formula (8) is a numerically expressed recurrence risk of a cancer in a cancer patient to be examined on the basis of expression levels and activity values of the first CDK and second CDK. As a result of examination of the relationship between the recurrence risk score RRS and the effect of the treatment by using an anthracycline-based anticancer drug in a cancer patient to be examined, close correlation between the two was recognized. Accordingly, the recurrence risk score RRS calculated by the formula (8) can be used as an indicator (judgment score S) for determining the effect of a treatment by using an anthracycline-based anticancer drug, to highly accurately determine the effect of a treatment by using an anthracycline-based anticancer drug.

Accordingly, the judgment score S for determining the effect of a treatment by using an anthracycline-based anticancer drug can be determined using the following formula:

$$S=F(x)\times G(y) \quad (10)$$

In the embodiment described above, a method for determining an effect of a treatment by using an anthracycline-based anticancer drug by calculating the judgment S and then comparing it with a threshold value has been described, but without limitation thereto, a method wherein an effect of a treatment by using an anthracycline-based anticancer drug is determined with another judgment criterion may be used.

For example, the method for determining an effect of a treatment by using an anthracycline-based anticancer drug can be constituted wherein the first CDK specific activity is calculated separately from the judgment score S; the judgment score S is used as a first judgment criterion and the first CDK specific activity is used as a second judgment criterion; and on the basis of the two judgment criteria, the effect of a treatment by using an anthracycline-based anticancer drug is determined.

Specifically, the expression levels and activity values of the first CDK and second CDK from a cancer patient to be examined are acquired, and the judgment score S and the first CDK specific activity are calculated, as described above.

Then, the judgment score S and the first CDK specific activity thus obtained are compared with the corresponding threshold values to determine the effect of a treatment by using an anthracycline-based anticancer drug.

More specifically, a first threshold value is set up as the threshold value for the judgment score S, and a second threshold value is set up as the threshold value for the first CDK specific activity, and when either the judgment score S or the first CDK specific activity obtained from the cancer patient to be examined is higher than the corresponding threshold value, the effect of a treatment by using an anthracycline-based anticancer drug is determined to be high, and when both the judgment score S and the first CDK specific activity are lower than the corresponding threshold values, the effect of a treatment by using an anthracycline-based anticancer drug is determined to be low.

Each of the first and second threshold values may contain two or more threshold values. For example, first threshold values a and b are previously set as the first threshold value, and second threshold values a and b are set as the second threshold value. Then, when the judgment score S is equal to or higher than the first threshold value a or when the first CDK specific activity is equal to or higher than the second threshold value a, the effect of a treatment by using an anthracycline-based anticancer drug is determined to be high; when the judgment score S is lower than the threshold value b and the first CDK specific activity is lower than the second threshold value b, the effect of a treatment by using an anthracycline-based anticancer drug is determined to be low; and when the first CDK specific activity is lower than the first threshold value a and is equal to or higher than the first threshold value b and simultaneously the first CDK specific activity is lower than the second threshold value a and is equal to or higher than the second threshold value b, the effect of a treatment by using an anthracycline-based anticancer drug is determined to be intermediate.

In this manner, the effect of a treatment by using an anthracycline-based anticancer drug can be determined more accurately by the judgment score S and another judgment criterion.

In this embodiment, there is provided a method for supporting a diagnosis of an effect of a treatment by using an anthracycline-based anticancer drug by displaying a judgment graph for determining the effect of a treatment by using an anthracycline-based anticancer drug.

Figure 2A:
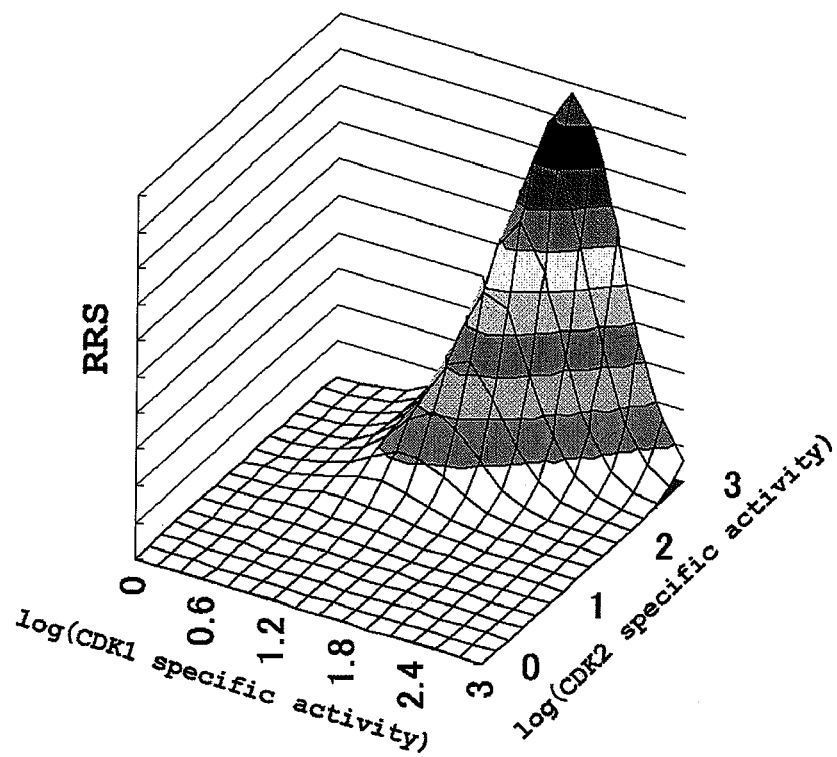
FIG. 2A is a three-dimensional graph showing a logarithm of CDK1 specific activity (x-axis), a logarithm of CDK2 specific activity (y-axis) and judgment score S (z-axis) as parameters.
Figure 2B:
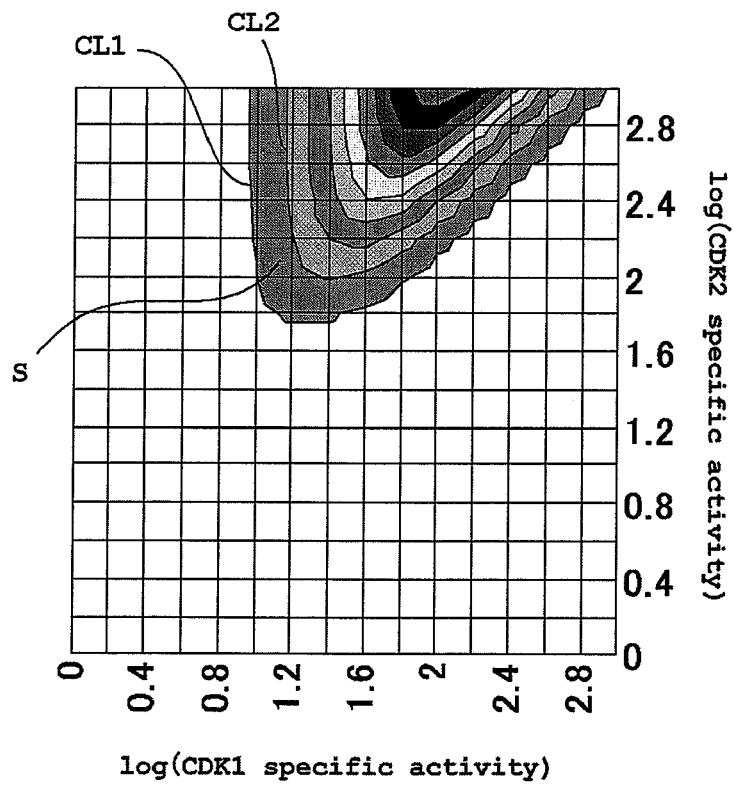
FIG. 2B is a two-dimensional projected plan of the judgment score S (z-axis) in FIG. 2A.

FIG. 2 is a view for schematically explaining the judgment score S described above. FIG. 2A is a three-dimensional graph with a logarithm of CDK1 specific activity (x-axis), a logarithm of CDK2 specific activity (y-axis), and judgment S (z-axis) as parameters. FIG. 2B is a two-dimensional projected plan of the judgment score S (z-axis) in FIG. 2A.

When the judgment score S is projected on a second-dimensional graph as shown in FIG. 2B, a plurality of contour curves each showing the same judgment score S are drawn.

For example, every point on curve CL1 is a point indicating the CDK1 and CDK2 specific activities giving the same judgment score S, and every point on curve CL2 is a point indicating the CDK1 and CDK2 specific activities giving the same judgment score S. Then, the zone surrounded by the curve is always a zone wherein the judgment score S is higher than on the curve (see FIG. 2A). For example, when the curve CL1 is a curve drawn by connecting points at which the judgment score S=M, the zone surrounded by the curve CL1 is a zone in which the judgment score S is equal to or higher than M. When the curve CL1 is a curve drawn by connecting points at which the judgment score S is a predetermined value M, and simultaneously the curve CL2 is a curve drawn by connecting points at which the judgment score S is a predetermined value N, the zone S surrounded by the curves CL1 and CL2 is a zone in which the relationship: M≦(judgment score S)<N is satisfied.

As described above, a two-dimensional graph consisting of the first CDK specific activity (x-axis) and the second CDK specific activity (y-axis) can be divided into zones that are made different in judgment score S by curves (cutoff lines) each being drawn by connecting point at which the judgment score S is the same.

The judgment graph for determining the effect of a treatment by using an anthracycline-based anticancer drug can be prepared in the following manner.

First, a threshold value is established for the judgment score S. The threshold value for the judgment score S may be a value that is effective in determining the effect of a treatment by using an anthracycline-based anticancer drug. The threshold value used herein is for example a value by which patients can be classified, depending on whether higher or lower than the threshold value, into those for whom treatment by using the anthracycline-based anticancer drug is effective and those for whom the treatment is not effective.

Then, a cutoff line is formed by connecting points at which the judgment score S is the threshold value, on the two-dimensional graph consisting of two parameters that are the first CDK specific activity and the second CDK specific activity, thereby dividing the two-dimensional graph into two zones wherein in one zone, the judgment score S is higher than the threshold value, and in the other zone, the judgment score S is lower than the threshold value. This cutoff line has been prepared on the basis of the value serving as a criterion for determination of the effect of a treatment by using an anthracycline-based anticancer drug, so the two-dimensional graph can be divided into zones having high and low effects of treatment by using an anthracycline-based anticancer drug respectively. The judgment graph for determining the effect of a treatment by using an anthracycline-based anticancer drug is prepared in this manner.

The first CDK specific activity and the second CDK specific activity calculated from the expression levels and activity values of the first CDK and second CDK obtained from a malignant tumor of a cancer patient to be examined are plotted on the judgment graph. The judgment graph has been divided by the cutoff line indicating the threshold value into the zones having high and low effects of a treatment by using an anthracycline-based anticancer drug respectively, so that when the first CDK specific activity and second CDK specific activity of the cancer patient to be examined are plotted on the judgment graph, whether the effect of a treatment by using an anthracycline-based anticancer drug in the patient is high or low can be determined at a glance. When the judgment graph is displayed, the medical doctor can determine the effect of a treatment by using an anthracycline-based anticancer drug in the cancer patient by glancing at the judgment graph, and can provide information useful in diagnosis of the effect of a treatment by using an anthracycline-based anticancer drug in the patient.

Figure 3:
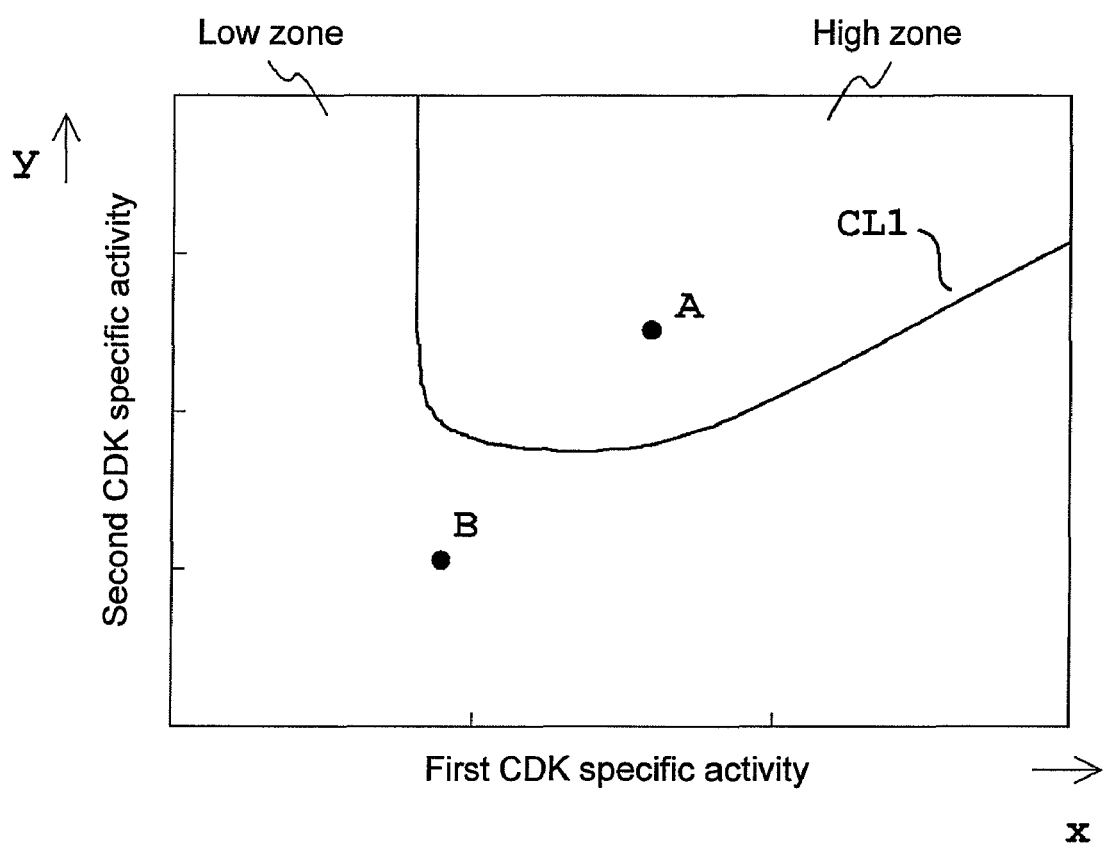
FIG. 3 is an example of judgment graph used in a supporting method in this embodiment.

FIG. 3 is an example of the judgment graph used in a method for supporting a diagnosis of an effect of a treatment by using an anthracycline-based anticancer drug according to this embodiment. This judgment graph shows the first CDK specific activity on the x-axis and the second CDK specific activity on the y-axis, wherein the distribution zone is divided by cutoff line CL1 into a zone wherein the effect of a treatment by using an anthracycline-based anticancer drug is high (High zone) and a zone wherein the effect of a treatment by using an anthracycline-based anticancer drug is low (Low zone).

Now, it is assumed that on the basis of the first CDK specific activity and the second CDK specific activity obtained from a certain cancer patient A, point A is plotted on the judgment graph. As shown in FIG. 3, the point A is placed in the high zone, so the effect of a treatment by using an anthracycline-based anticancer drug can be determined to be high for the patient A.

Similarly, it is assumed that on the basis of the first CDK specific activity and the second CDK specific activity obtained from a certain cancer patient B, point B is plotted on the judgment graph. As shown in FIG. 3, the point B is placed in the low zone, so the effect of a treatment by using an anthracycline-based anticancer drug can be determined to be low for the patient B.

The judgment graph that can be used to determine the effect of a treatment by using an anthracycline-based anticancer drug may be a judgment graph in a different mode depending on the intended use.

Figure 4:
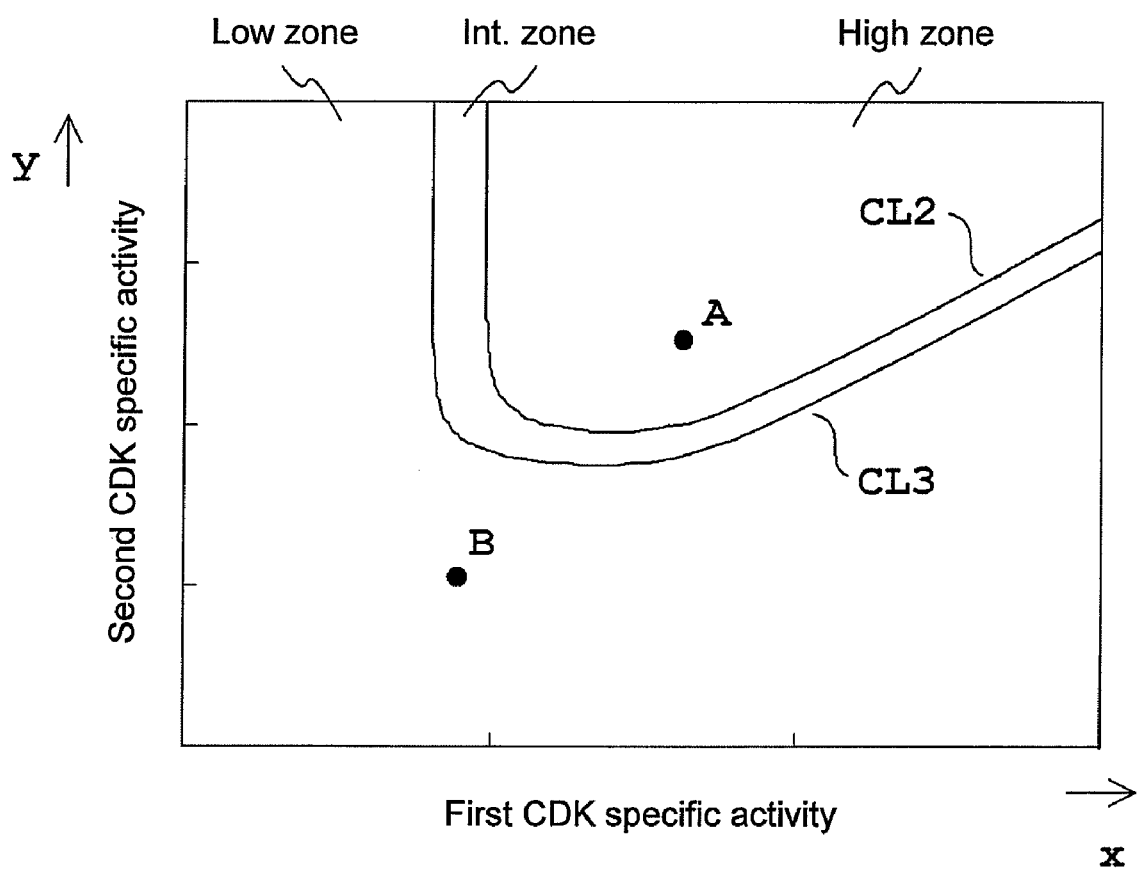
FIG. 4 is another example of judgment graph used in a supporting method in this embodiment.

FIG. 4 is another example of the judgment graph used in a method for supporting a diagnosis of an effect of a treatment by using an anthracycline-based anticancer drug according to this embodiment. This judgment graph shows the first CDK specific activity on the x-axis and the second CDK specific activity on the y-axis, wherein the distribution zone is divided by cutoff lines CL2 and CL3 into 3 zones, that is, a zone wherein the effect of a treatment by using an anthracycline-based anticancer drug is high (high zone), a zone wherein the effect of a treatment by using an anthracycline-based anticancer drug is low (Low zone), and a zone wherein the effect is intermediate (Int. zone).

By using the judgment graph divided into 3 or more regions, the effect of a treatment by using an anthracycline-based anticancer drug in cancer patients to be examined can be determined in grades.

Figure 5:
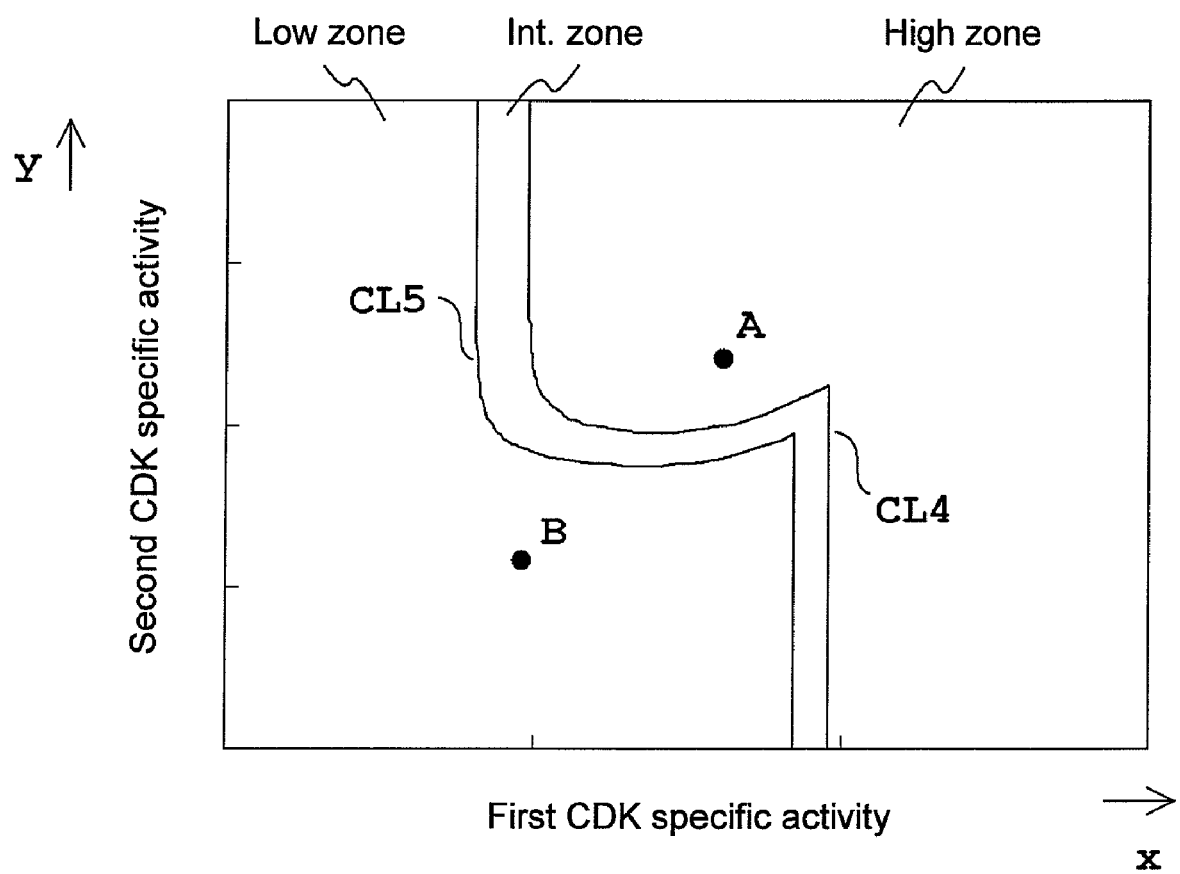
FIG. 5 is another example of judgment graph used in a supporting method in this embodiment.

FIG. 5 is another example of the judgment graph used in a method for supporting a diagnosis of an effect of a treatment by using an anthracycline-based anticancer drug according to this embodiment. This judgment graph is divided into 3 zones, that is, a zone wherein the effect of a treatment by using an anthracycline-based anticancer drug is high (High zone), a zone wherein the effect of a treatment by using an anthracycline-based anticancer drug is low (Low zone), and a zone wherein the effect is intermediate (Int. zone), by cutoff lines CL4 and CL5 formed by connecting the curve wherein the judgment score S is a threshold value, to the line wherein the first CDK specific activity is a threshold value.

By using the judgment graph based on the judgment score S and the first CDK specific activity, the effect of a treatment busing an anthracycline-based anticancer drug in cancer patients to be examined can be more accurately determined.

[2] Judgment Device

Then, the device for determining an effect of a treatment by using an anthracycline-based anticancer drug in this embodiment is described.

Figure 6:
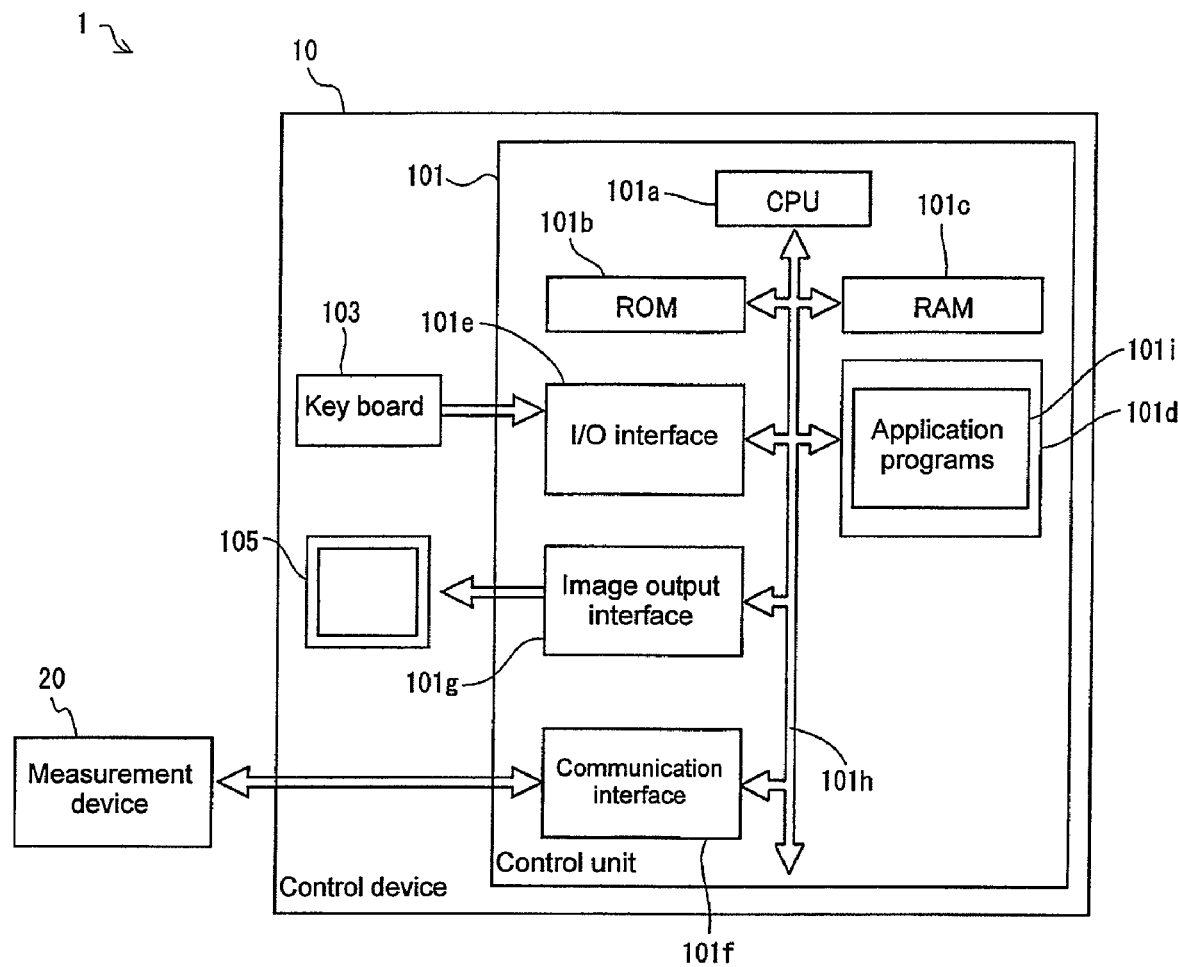
FIG. 6 is a block diagram showing a framework of the judgment device in this embodiment.

FIG. 6 is a block diagram showing a skeleton framework of the judgment device in this embodiment. The judgment device 1 in this embodiment is a device for determining an effect of a treatment by using an anthracycline-based anticancer drug in a cancer patient to be examined, on the basis of data obtained from the cancer patient, and is composed of a control device 10 and a measurement device 20 as shown in FIG. 6. The control device 10 is a device that analyzes measurement data output by the measurement device 20 to judge a risk of cancer recurrence and outputs the judgment result, and the measurement device 20 is a device that measures a malignant tumor collected from a cancer patient to be examined and outputs the measurement data to the control device 10.

The control device 10 comprises a personal computer (PC) and includes a control unit 101, a keyboard 103 and a display unit 105. The control unit 101 includes CPU 101a, ROM 101b, RAM 101c, a hard disk 101d, an input/output (I/O) interface 101e, a communication interface 101f, an image output interface 101g, and bus 101h, and the respective parts are connected to one another via bus 101h to mutually transmit and receive data.

The CPU 101a can execute computer programs stored in the ROM 101b and computer programs loaded on the RAM 101c. The ROM 101b stores computer programs executed by the CPU 101a and data for executing these computer programs. The RAM 101c is used to read computer programs stored in the ROM 101b and hard disk 101d. The RAM 101c is also used as a work area for the CPU 101a when executing these computer programs.

Installed in the hard disk 101d are various computer programs to be executed by the CPU 101a such as an operating system (OS) and application programs, and various data used for executing these computer programs.

Also installed on the hard disk 101d is the application program 101i which comprises an application program for realizing the present method for determining an effect of a treatment by using an anthracycline-based anticancer drug.

An I/O interface 101e has a keyboard 103 and a mouse (not shown) connected thereto. A communication interface 101f has the measurement device 20 connected thereto, and via the communication interface 101f, data can be transmitted and received between the control unit 101 and the measurement device 2.

The image output interface 101g is connected to the display unit 105 and outputs an image signal corresponding to image data given by CPU 101a to the display unit 105. The display unit 105 displays an (on-screen) image according to the input image signal.

The measurement device 20 connected via the communication interface 101f to the control device 10 is a device for measuring the expression level and activity value of CDK from a biological tissue. A conventionally known device for judging tissue properties can be used as a measurement device for measuring the CDK expression level and CDK activity value from a biological tissue.

US 2007/0077658 is hereby incorporated by reference in its entirely as though fully and completely set forth herein.

In this embodiment, the judgment device 1 is constituted so as to receive measurement data obtained by the measurement device 20 and to determine, on the basis of the measurement data, the effect of a treatment by using an anthracycline-based anticancer drug in a cancer patient to be examined, but may, without limitation to such constitution, be constituted such that measurement data on the previously measured CDK expression level and CDK activity value are inputted via the keyboard 103.

Figure 7:
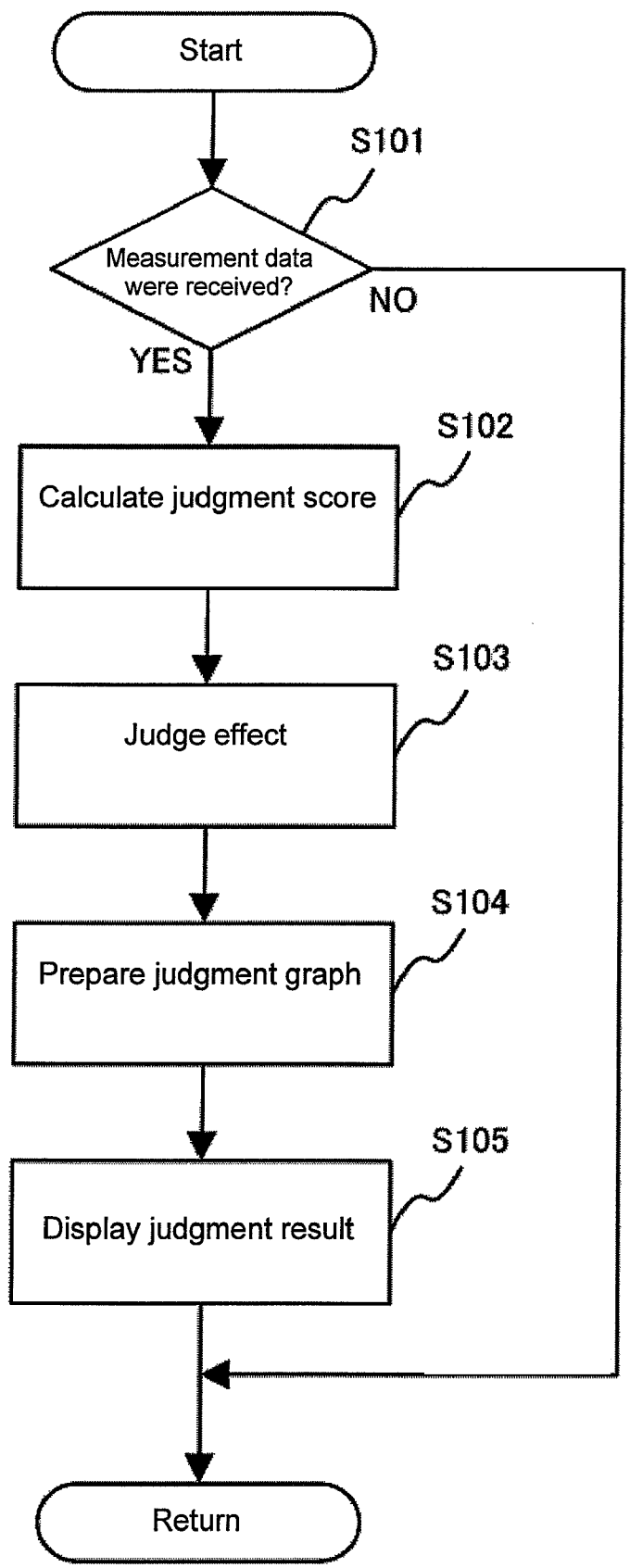
FIG. 7 is a flowchart showing a processing for judging an effect of a treatment by using an anthracycline-based anticancer drug with the judgment device in this embodiment.

FIG. 7 is a flowchart showing processing for determining the effect of a treatment by using an anthracycline-based anticancer drug by the judgment device 1 in this embodiment.

To realize the processing according to this flowchart, the application program 101i installed in the hard disk 101d is read by RAM 101c, and the CPU 101a executes the application program 101i read by the RAM 101c.

First in step S101, CPU 101a executes processing for judging whether measurement data are received or not from the measurement device 20. When CPU 101a judges that measurement data from the measurement device 20 are not received (NO in step S101), the processing is returned.

As used herein, the measurement data refer to the expression levels and activity values of at least two CDKs obtained by measuring a biological tissue with the measurement device 20.

When CPU 101a judges that measurement data from the measurement device 20 are received (YES in step S101), the processing advances to step S102 in which CPU101a executes processing that calculates the judgment score S.

The formula for calculating judgment score S based on the first CDK and second CDK expression levels and activity values as described in the method for determining the effect of a treatment by using an anthracycline-based anticancer drug is integrated in the application program 101i, and the CPU 101a executes the application program 101i, thereby calculating the judgment score S.

Then, the processing advances to step S103, and the CPU 101a executes processing for determining the effect of a treatment by using an anthracycline-based anticancer drug. This processing is carried out by comparing the judgment score S calculated in step S102 with a predetermined threshold value set up in the application program 101i.

By CPU 101a, the effect of a treatment by using an anthracycline-based anticancer drug is determined to be "high" when the judgment score S is equal to or higher than the predetermined threshold value, or the effect of a treatment by using an anthracycline-based anticancer drug is determined to be "low" when the judgment score S is lower than the predetermined threshold value.

Then, the processing advances to step S104, and the CPU 101a executes processing for preparing a judgment graph.

The judgment graph is a two-dimensional graph consisting of two parameters, i.e. the first CDK specific activity and the second CDK specific activity as described in the method for determining the effect of a treatment by using an anthracycline-based anticancer drug, wherein the distribution zone is divided into zones different in the effect of a treatment by using an anthracycline-based anticancer drug. This two-dimensional graph is divided into a zone wherein the effect of a treatment by using an anthracycline-based anticancer drug is high and a zone wherein the effect is low, by the cutoff line drawn by connecting points at which the judgment score S is the predetermined threshold value. Samples that have been measured for the effect of a treatment by using an anthracycline-based anticancer drug are plotted on this two-dimensional graph.

The processing then advances to step S105, and the CPU 101a executes processing in which the effect judgment result of obtained in step S103, and the judgment graph prepared in step S105, are displayed on the display unit 105.

Figure 8:
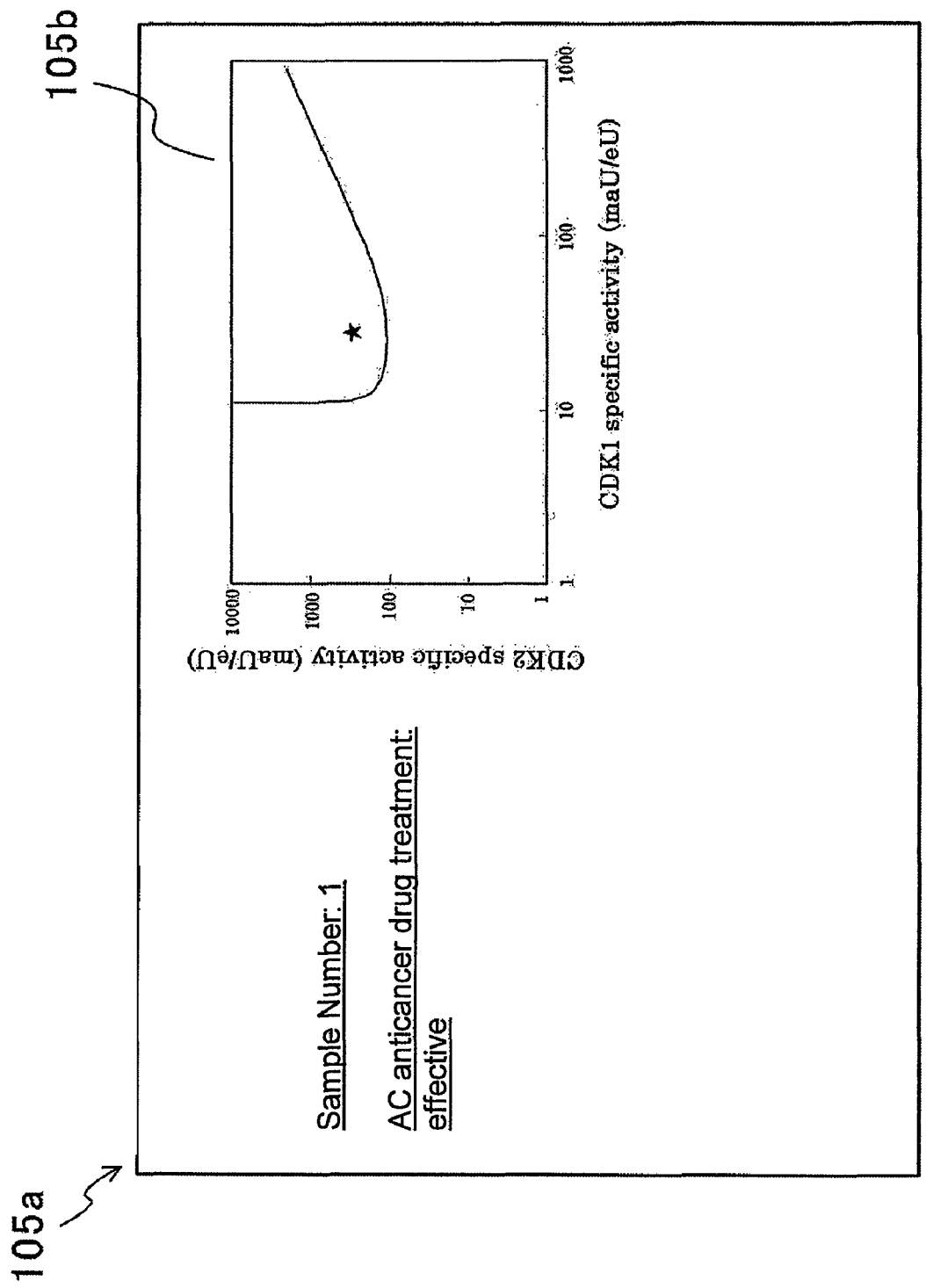
FIG. 8 is an example of a judgment result on a display of the judgment device in this embodiment.

FIG. 8 is a graph showing an example of a non-screen judgment result. As shown in the figure, the judgment result display 105a on the display unit 105 displays the sample number of a sample which has been judged, the judgment result of effect, and the judgment graph 105b.

The judgment graph 105b is a two-dimensional graph prepared in step S105, and the CDK1 specific activity and CDK2 specific activity of the sample which has been measured for the effect of a treatment by using an anthracycline-based anticancer drug are plotted and displayed (shown by the mark of star in the graph). By showing the judgment graph together with the judgment result of effect based on the judgment score S, the effect in the cancer patient to be examined can be visually known.

The display that displays the judgment graph 105b on which only samples examined for the effect were plotted has been described, but may, without limitation to such constitution, be constituted so as to display a judgment graph on which a plurality of samples including both samples from cancer patients for whom the treatment with an anthracycline-based anticancer drug was effective and samples from cancer patients for whom the treatment with an anthracycline-based anticancer drug was not effective are plotted. Given such constitution, the display can also provide statistical information on the effect of a treatment by using an anthracycline-based anticancer drug.

EXAMPLE

The judgment method according to this embodiment was used to determine the effect of a treatment by using an anthracycline-based anticancer drug in cancer patients.

From cancer patients who after excision of malignant tumors, were administered with an anthracycline-based anticancer drug, malignant tumors were collected before administration with the anthracycline-based anticancer drug, and the expression levels and activity values of CDK1 and CDK2 in the malignant tumors were measured.

The obtained expression levels and activity values of CDK1 and CDK2 were used to calculate the judgment score S based on the following formula (11) to (13):

$$RS1; F(x) = 0.18/(1 + \mathrm{Exp}(-(x-1.6) \times 7)) \quad (11)$$

$$RS2; G(y) = 0.25/(1 + \mathrm{Exp}(-(y-1.0) \times 6)) \quad (12)$$

$$S = 2500 \times F(x) \times G(y) \quad (13)$$

x = CDK1 activity value/CDK1 expression level
y = (CDK2 activity value × CDK1 expression level)/(CDK2 expression level × CDK1 activity value)

Then, the judgment score S obtained form each case was compared with the following conditions, to classify the cancer patients into a group for whom the effect of a treatment by using an anthracycline-based anticancer drug was high (High group) and a group for whom the effect was low (Low group).
High group: $S \geq 2.3$ and
Low group: $S < 2.3$ In each patient group, the number of patients who underwent recurrence within 5 years and the accumulative recurrence rate in each patient group within 5 years were calculated. The results are shown in Table 1.

TABLE 1

| Group | Number of patients | Number of patients with recurrence | Accumulative recurrence rate within 5 years |
|---|---|---|---|
| High | 11 | 1 | 10.0% |
| Low | 38 | 15 | 40.3% |
| Total | 49 | 16 | 33.6% |

As shown in Table 1, the result of classification of cancer patients by the judgment method in this embodiment revealed that the number of patients in High group was 11, the number of patients in Low group was 38, and the numbers of patients who underwent recurrence within 5 years in the two groups were 1 and 15, respectively. The accumulative recurrence rate in each patient group within 5 years was 10.0% in High group and 40.3% in Low group, thus revealing that the survival rate of the patients without recurrence within 5 years is significantly higher in High group than in Low group. Since the accumulative recurrence rate within 5 years in the total cancer patients to be examined is 33.6%, it can be seen that the survival rate without recurrence in the cancer patients in High group is high even compared with the total cancer patients to be examined.

That is, it can be said from the number in "Total" in Table 1 that when the anthracycline-based anticancer drug is administered without depending on the judgment method in this embodiment, about 37% patients cannot receive its effective anticancer treatment, merely resulting in undergoing its side effects.

According to the judgment method in this embodiment, on the other hand, at least cancer patients classified in High group can be provided at a high probability of about 90% with the effective anticancer treatment by using an anthracycline-based anticancer drug.

From this result, the cancer patients for whom the effect of a treatment by using an anthracycline-based anticancer drug had been determined to be high by the judgment method of the present invention were effectively prevented from undergoing cancer recurrence by administering an anthracycline-based anticancer drug, and it was thus demonstrated that the effect of a treatment by using an anthracycline-based anticancer drug in cancer patients can be highly accurately determined.

This judgment result can be also obtained by the judgment method using the judgment graph in this embodiment. The judgment result is as follows.

First, the expression levels and activity values of CDK1 and CDK2 in the cancer patients in this example were used to calculate the CDK1 specific activity and CDK2 specific activity of each cancer patient, according to the following formulae (14) and (15):

CDK1 specific activity=CDK1 activity value/CDK1 expression level (14)

CDK2 specific activity=CDK2 activity value/CDK2 expression level (15)

Figure 9:
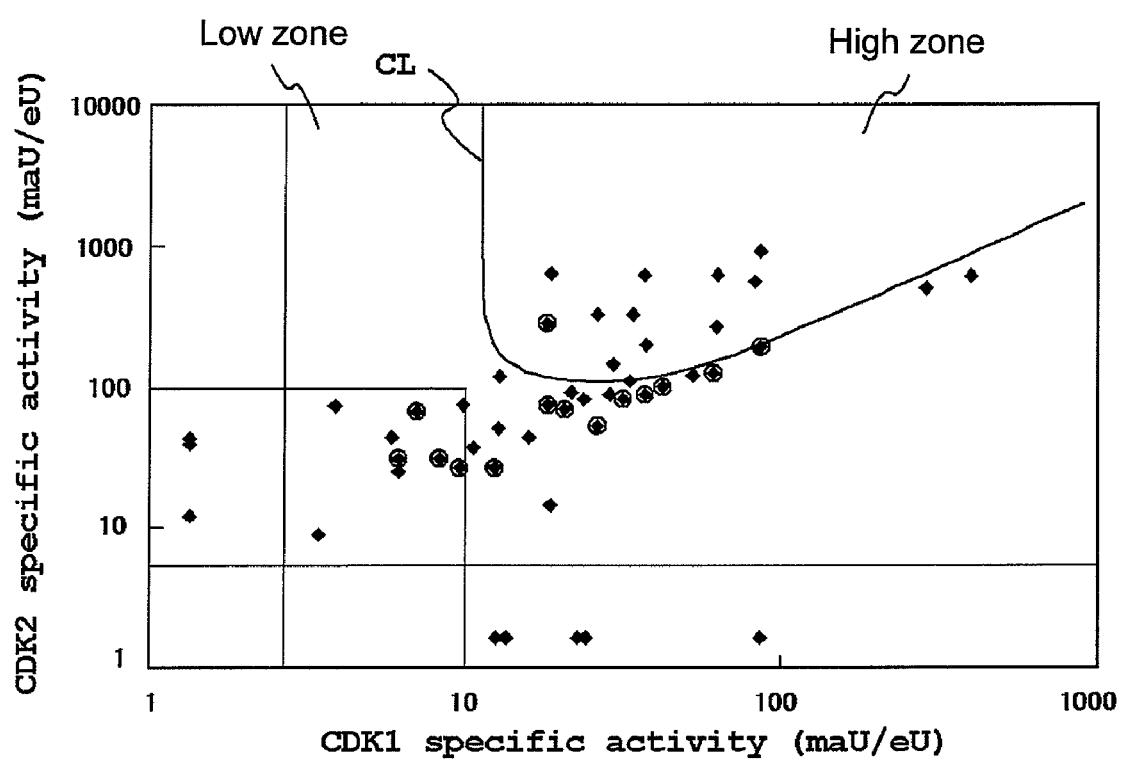
FIG. 9 is a two-dimensional graph on which cancer patients in this example are plotted on basis of CDK1 specific activity (x-axis) and CDK2 specific activity (y-axis).

Based on the CDK1 specific activity and CDK2 specific activity thus obtained, the cancer patients were then plotted on a two-dimensional graph consisting of two parameters, i.e. CDK1 specific activity and CDK2 specific activity, as shown in FIG. 9.

FIG. 9 is a two-dimensional graph on which the cancer patients in this example are plotted based on the CDK1 specific activity (x-axis) and CDK2 specific activity (y-axis), wherein the cancer patients are divided by cutoff line CL into a group of the cancer patients for whom the effect of a treatment by using an anthracycline-based anticancer drug is high (High group) and a group of the cancer patients for whom the effect is low (Low group).

In FIG. 9, the cutoff line CL is a curve drawn by connecting points at which the judgment score S determined based on the CDK1 specific activity and CDK2 specific activity is 2.3.

In this graph, the patients who underwent cancer recurrence within 5 years after extirpation of malignant tumor are shown by circling.

As a result of classification of the patient groups with the judgment graph, the same classification results as in Table 2 were obtained. From this result, it was demonstrated that the effect of a treatment by using an anthracycline-based anticancer drug in cancer patients can be suitably determined by using the recurrence risk judgment graph in this embodiment.

Accordingly, it was suggested that the judgment graph in this embodiment can be displayed to provide information for supporting a diagnosis of a highly reliable effect of a treatment by using an anthracycline-based anticancer drug.

What is claimed is:

1. A method for supporting a diagnosis of an effect of a treatment by using anthracycline anticancer drugs, comprising:
measuring in a malignant tumor sample collected from a patient an expression level of a cyclin dependent kinase 1 (CDK1), an activity value of the CDK1, an expression level of a CDK2 and an activity value of the CDK2 by using a measuring apparatus; and
calculating by a computer a judgment score based on the following formula (1), judgment score=$F(x) \times G(y)$ (1)

wherein x represents a CDK1 specific activity which is able to be calculated by using a ratio of the expression level and the activity value of the CDK1, and y represents a specific activity ratio which is able to be calculated by using a ratio of the CDK1 specific activity and a CDK2 specific activity wherein the CDK2 specific activity is able to be calculated by using a ratio of the expression level and the activity value of the CDK2.

2. The method of claim 1 further comprising judging an effect of a treatment by using anthracycline anticancer drugs based on the calculated judgment score.

3. The method of claim 2, wherein the judgment of an effect is conducted by comparing the judgment score with a predetermined threshold value.

4. The method of claim 3, wherein in the judgment of the effect, the effect is judged to be high when the judgment score is equal to or higher than the predetermined threshold value, and the effect is judged to be low when the judgment score is lower than the predetermined threshold value.

5. A method for supporting a diagnosis for an effect of a treatment by using anthracycline anticancer drugs, comprising:
measuring in a malignant tumor sample collected from a patient an expression level of a cyclin dependent kinase 1 (CDK1), an activity value of the CDK1, an expression level of a CDK2 and an activity value of the CDK2 by using a measuring apparatus;
calculating by a computer a CDK1 specific activity which is able to be calculated by using a ratio of the expression level and the activity value of the CDK1, and a CDK2 specific activity which is able to be calculated by using a ratio of the expression level and the activity value of the CDK2; and
displaying on a display unit a judgment graph which comprises at least two parameters of a CDK1 specific activity and a CDK2 specific activity, and is divided into zones different in judgment score calculated based on following formula (4),
wherein the cancer patient to be examined is plotted based on the CDK1 specific activity and the CDK2 specific activity on the judgment graph, judgment score=$F(x) \times G(y)$ (4)

wherein x represents a CDK1 specific activity; and y represents a specific activity ratio which is able to be calculated by using a ratio of the CDK1 specific activity and the CDK2 specific activity.

6. The method of claim 5, further comprising:
judging an effect of a treatment by using anthracycline anticancer drugs based on the judgment graph and the plotted cancer patient to be examined; and
displaying the judgment results together with the judgment graph.

7. The method of claim 6, wherein the judgment is conducted by determining which zone of the judgment graph the cancer patient to be examined is plotted on.

8. A device of supporting a diagnosis of an effect of a treatment by using anthracycline anticancer drugs, comprising:
a measuring apparatus for measuring a malignant tumor collected from a cancer patient to be examined to acquire an expression level of a cyclin dependent kinase 1 (CDK1), an activity value of the CDK1, an expression level of a CDK2 and an activity value of the CDK2; and a controller including a memory under the control of a processor, the memory storing instructions enabling the processor to carry out operations which comprise calculating a judgment score based on the following formula (5):

$$\text{judgment score} = F(x) \times G(y) \qquad (5)$$

wherein x represents a CDK1 specific activity which is able to be calculated by using a ratio of the expression level and the activity value of the CDK1, and y represents a specific activity ratio which is able to be calculated by using a ratio of the CDK1 specific activity and the CDK2 specific activity wherein the CDK2 specific activity is able to be calculated by using a ratio of the expression level and the activity value of the CDK2.

9. The device of claim 8, wherein the operations further comprise judging an effect of a treatment by using anthracycline anticancer drugs based on the calculated judgment score.

10. The device of claim 9, wherein the judgment of the effect is conducted by comparing the judgment score with a predetermined threshold value.

11. The device of claim 10, wherein in the judgment of the effect, the effect is judged to be high when the judgment score is equal to or higher than the predetermined threshold value, and the effect is judged to be low when the judgment score is lower than the predetermined threshold value.

12. A device for supporting a diagnosis of an effect of a treatment by using anthracycline anticancer drugs, comprising:

a measuring apparatus for measuring a malignant tumor collected from a cancer patient to be examined to acquire an expression level of a cyclin dependent kinase 1 (CDK1), an activity value of the CDK1, an expression level of a CDK2 and an activity value of the CDK2;

a display; and a controller including a memory under the control of a processor, the memory storing instructions enabling the processor to carry out operations comprising: calculating a CDK1 specific activity and a CDK2 specific activity of the cancer patient to be examined based on the measurement results by the measurement section, wherein the CDK1 specific activity is able to be calculated by using a ratio of the expression level and the activity value of the CDK1, and the CDK2 specific activity is able to be calculated by using a ratio of the expression level and the activity value of the CDK2; and displaying a judgment graph which comprises at least two parameters of a CDK1 specific activity and a CDK2 specific activity, and is divided into zones different in judgment score calculated based on following formula (8), wherein the cancer patient to be examined is plotted based on the CDK1 specific activity and the CDK2 specific activity on the judgment graph, $$\text{judgment score} = F(x) \times G(y) \qquad (8)$$

wherein x represents a CDK1 specific activity, and y represents a specific activity ratio which is able to be calculated by using a ratio of the CDK1 specific activity and the CDK2 specific activity.

13. The device of claim 12, wherein the operations further comprises:

judging an effect of a treatment by using anthracycline anticancer drugs, based on the judgment graph and the plotted cancer patient to be examined; and displaying the judgment results together with the judgment graph.

14. The device of claim 12, wherein the judgment of the effect is conducted by determining which zone of the judgment graph the cancer patient to be examined is plotted on.

* * * * *